(12) United States Patent
Huang et al.

(10) Patent No.: US 7,368,082 B1
(45) Date of Patent: May 6, 2008

(54) FORMULATION OF SPOTTING SOLUTION TO ACHIEVE UNIFORM SPOT SIZE AND MORPHOLOGY AND FOR NONDESTRUCTIVE QUALITY CONTROL OF ASSAY ARTICLES

(76) Inventors: Tung-Lian Huang, 1206 Eckenrode, Placentia, CA (US) 92870; Daniel Keys, 8 Cresthaven, Irvine, CA (US) 92604; M. Parameswara Reddy, 219 Valverde, Brea, CA (US) 92821

( * ) Notice: Subject to any disclaimer, the term of this patent is extended or adjusted under 35 U.S.C. 154(b) by 212 days.

(21) Appl. No.: 10/317,950

(22) Filed: Dec. 12, 2002

(51) Int. Cl.
*G01N 15/06* (2006.01)
*G01N 33/00* (2006.01)
*G01N 33/48* (2006.01)

(52) U.S. Cl. .................. 422/68.1; 422/82.05; 427/9; 427/157

(58) Field of Classification Search .................. 435/6, 435/14, 7.1, 4; 436/523, 518, 501; 106/31.13, 106/31.15; 422/50, 68.1, 82.07, 82.05; 427/9, 427/157
See application file for complete search history.

(56) References Cited

U.S. PATENT DOCUMENTS

| | | | | |
|---|---|---|---|---|
| 4,621,049 A | * | 11/1986 | Wang | 435/14 |
| 4,921,787 A | * | 5/1990 | Riggin et al. | 435/5 |
| 5,677,197 A | * | 10/1997 | Gordon et al. | 436/518 |
| 5,897,695 A | * | 4/1999 | Mayo et al. | 106/31.75 |
| 5,994,065 A | * | 11/1999 | Van Ness | 435/6 |
| 6,248,521 B1 | * | 6/2001 | Van Ness et al. | 435/6 |
| 6,342,349 B1 | * | 1/2002 | Virtanen | 435/6 |
| 6,376,619 B1 | * | 4/2002 | Halverson et al. | 525/330.3 |
| 6,730,521 B1 | * | 5/2004 | Cassells | 436/523 |
| 2003/0108897 A1 | * | 6/2003 | Drmanac | 435/6 |
| 2003/0170672 A1 | * | 9/2003 | Cho et al. | 435/6 |

FOREIGN PATENT DOCUMENTS

WO    WO 02/27026    *    4/2002

OTHER PUBLICATIONS

Lindroos et al. Minisequencing on oligonucleotide microarrays: comparison of immobilisation chemistries. 2001, Nucleic Acids Research, vol. 29, No. 13, pp. 1-7.*

* cited by examiner

*Primary Examiner*—Long V. Le
*Assistant Examiner*—Melanie J. Yu
(74) *Attorney, Agent, or Firm*—Michael C. Schiffer

(57) ABSTRACT

This invention relates to spotting solutions for the production of assay articles with uniform spot size and morphology for the detection of biopolymers, comprising N-lauroyl sarcosine in a buffered solution. Optionally the spotting solution may further comprise a fluorophore or a dye. This invention further provides means for non-destructive quality control of the production of said assay articles. This invention further provides means for non-destructive quality control of the production of said assay articles.

6 Claims, 8 Drawing Sheets

The assay images of spots printed with spotting solution containing 0%, 0.0015% or 0.045% (w/v) of N-lauroyl sarcosine (NLS) in 45 mM borate buffer at pH 9.3.

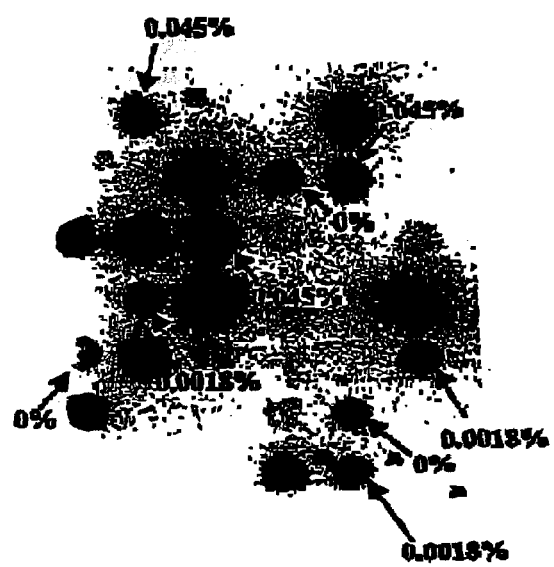
Figure 1. The assay images of spots printed with spotting solution containing 0%, 0.0018% or 0.045% (w/v) of N-lauroyl sarcosine (NLS) in 45 mM borate buffer at pH 9.3.

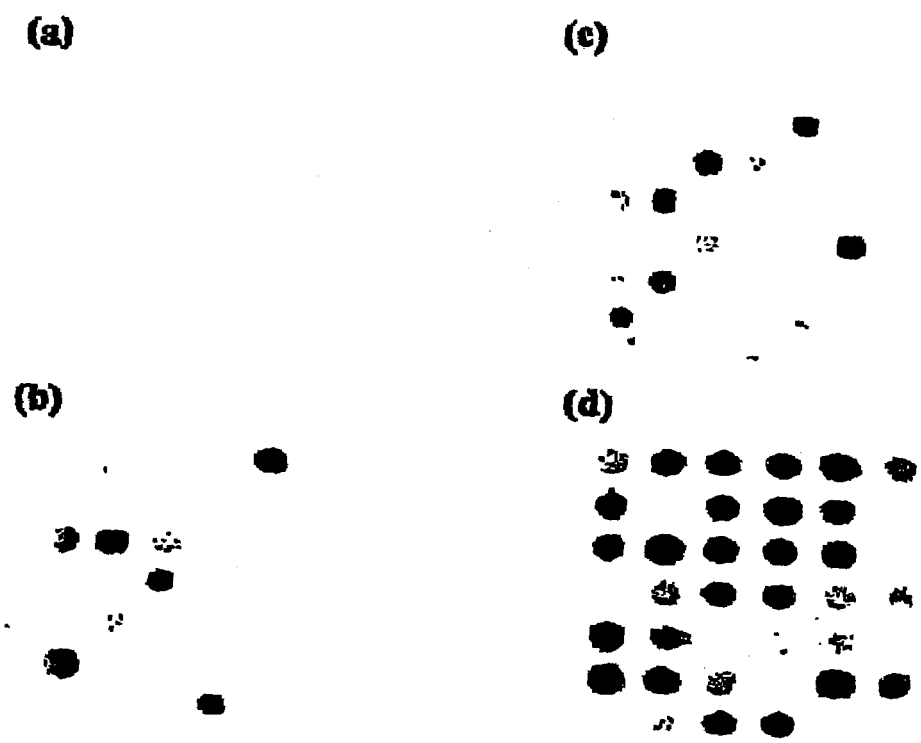
Figure 2. The assay images of spots printed with 45 mM borate buffer (pH 9.3) containing a) 10%, 20%, or 30% of formamide, b) 1%, 2%, or 4% of betaine, c) 0%, 10%, 20% of DMSO, d) 0.0018% (w/v) of N-lauryl sarcosine (NLS).

(a)
(b)
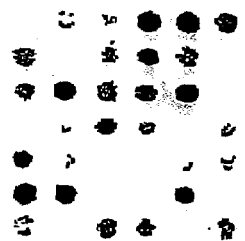
Figure 3. The assay images of spots printed various commercial formulations of spotting solution, including a) MicroSpotting Solution Plus®, pH 9.5. b) 0.0018% (w/v) of N-lauroyl sarcosine (NLS) in 45 mM borate buffer, pH 9.3.

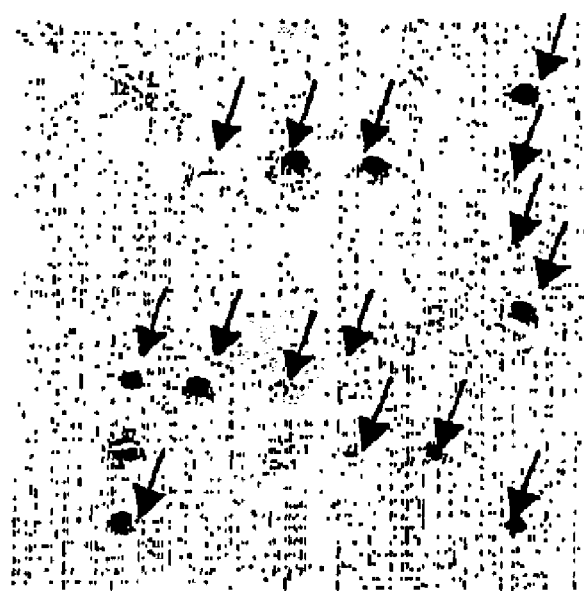
Fig. 3(c): The red arrows indicate the spots printed with Aldehyde spotting solution.

(a)
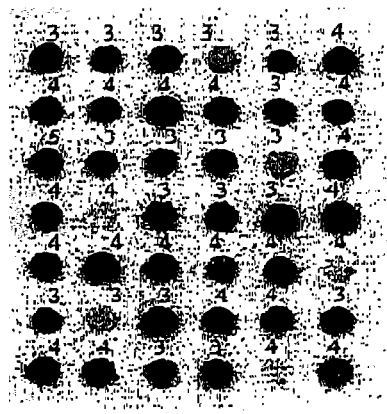
(b)
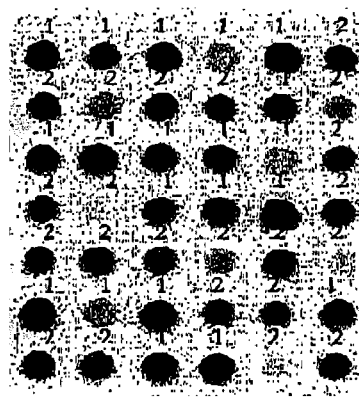
Figure 4. The assay images of spots printed with the spotting solutions containing 0.0018% (w/v) of N-lauroyl sarcosine (NLS) in 45 mM borate buffer at a) pH10 or 10.5 and b) pH8.5 or 9.3. The numbers 1-4 indicate the pH's of the solutions as 1 indicating pH 8.5, 2 indicating pH 9.3, 3 indicating pH 10, and 4 indicating pH 10.5

Figure 5. The assay images of spots printed with the spotting solution containing 0.0015% (w/v) of N-lauroyl sarcosine (NLS) in 45 mM borate buffer at pH 9.3. After printing, the microarrays were incubated at room temperature with a) 70% RH (relative humidity) or b) 95% RH.

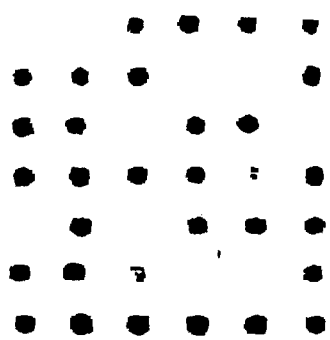
Figure 6. The assay images of spots printed with the use of a contact pin arrayer. The spotting solution was 0.00018% (w/v) of N-lauroyl sarcosine (NLS) in 45 mM borate buffer at pH 9.3.

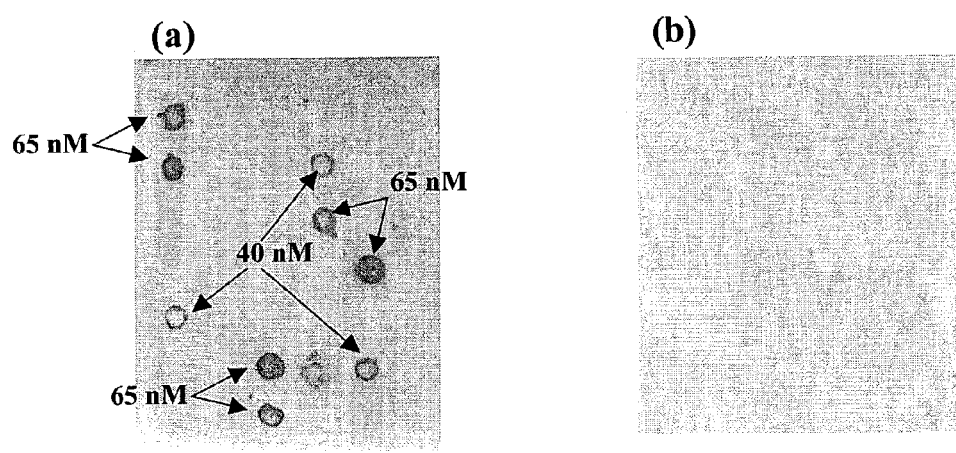

Figure 7. The images of dispensed spots printed with the spotting solution containing 40 nM or 65 nM of fluorecein dye in 0.0018% (w/v) of N-lauroyl sarcosine (NLS), 45 mM borate buffer at pH 9.3. The spots were imaged at the emission wavelength of fluorescein (~525 nm). (a): The microarray was imaged immediately after the arraying process. (b): The microarray was imaged after rinsed with a washing solution containing 0.1% casein and 0.15 M NaCl in 50 mM carbonate buffer, followed by water rinse.

FORMULATION OF SPOTTING SOLUTION TO ACHIEVE UNIFORM SPOT SIZE AND MORPHOLOGY AND FOR NONDESTRUCTIVE QUALITY CONTROL OF ASSAY ARTICLES

FIELD OF THE INVENTION

This invention relates to reagents and methods for rapidly assaying the presence of biopolymers in samples. More particularly, this invention provides spotting solutions for the production of assay articles, including microarrays, having uniform spot size and morphology for the detection of biopolymers. This invention further relates to means for non-destructive quality control of assay article production.

BACKGROUND OF THE INVENTION

Analysis of unknown biopolymer targets often involves their specific binding to known biopolymer probes. The most common technique employing immobilized biopolymers is the Southern blot hybridization technique, in which a set of DNA targets is immobilized on a membrane and a solution containing labeled DNA probe molecules is used to bathe the membrane under conditions where complementary molecules will anneal. In an analogous technique called Northern blot hybridization, RNA targets are immobilized on membranes and anneal to complementary RNA probes. Reverse blot hybridization employs the opposite approach. Instead of immobilizing DNA targets, a set of DNA probes is immobilized on a solid surface and the unknown labeled DNA target is present in the liquid phase.

Arrays, constructed by attaching a plurality of the same or different biopolymers to discrete isolated areas on the surface of a substrate, are becoming increasingly important tools in the analysis of biopolymers such as gene expression analysis, DNA sequencing, mutation detection, polymorphism screening, linkage analysis, genotyping, and screening for alternative splice variants in gene transcripts.

The analysis of microarrays depends considerably on spot quality, such as morphology and homogeneity, for obtaining high levels of accuracy and consistency. Quality control of common printing defects generated during the production of an array is critical to maintaining data integrity and preventing the wastage of reagent and labor. The ability to manufacture microarrays in an efficient and cost-effective manner is of considerable interest to researchers worldwide and of significant commercial value.

One important factor in the spotting process is the chemical properties of the solution in which the biopolymer is dissolved. With the widely used saline sodium citrate (SSC) buffer, binding efficiency and spot uniformity are often poor. The problems are reduced by supplementing SSC with 50% dimethyl sulfoxide (DMSO). However, this reaction buffer has the disadvantage of being toxic as well as being a solvent for many materials, in addition to only having a limited effect on spot appearance.

Considering the issues of spot morphology and quality control in spot arraying, there is still a need for a formulation of a spotting solution that will provide uniform spot size and/or morphology in the production of assay articles such as microarrays. There also remains a need for a means of non-destructive quality control of the production of such assay articles.

SUMMARY OF THE INVENTION

Accordingly, this invention provides a cost-efficient, rapid and convenient method of making an assay article and a method of using such an assay article for biopolymer detection. More particularly, this invention provides spotting solutions for the production of assay articles with uniform spot size and morphology for the detection of biopolymers. This invention further provides means for non-destructive quality control of the production of said assay articles.

The present invention is based on the discovery that spotting solutions comprising N-lauroyl sarcosine provide assay articles having superior uniformity in spot size and morphology compared to conventional spotting solutions.

Accordingly, one aspect of this invention provides spotting solutions for dispensing biopolymers onto the surface of a substrate, said spotting solution comprising N-lauroyl sarcosine or an equivalent thereof in a buffered solution. The buffer can be acidic, neutral, or basic, and the selection of the pH of the buffer is based on the method or chemistry used to immobilize the biopolymer to the substrate.

In addition, this invention is based on the discovery that the inclusion of a fluorophore or a dye in the spotting solutions of this invention provides a means for non-destructive quality control of assay article production, in that the fluorophore or dye does not interfere with the adsorption of the biopolymer to the surface of the substrate or with subsequent assay steps. Therefore, in certain embodiments the spotting solutions of this invention further comprise a fluorophore or a dye. Examples of suitable fluorophores include, but are not limited to, fluorescein and derivatives thereof, and rhodamine and derivatives thereof. An example of a dye suitable for purposes of this invention includes, but is not limited to, xylene cyanol. An example of a spotting solution of this invention comprises 0.0018% (w/v) N-lauroyl sarcosine and 65 nM fluorescein in 45 nM borate buffer at pH 9.3. Another example of a spotting solution of this invention comprises 0.0018% (w/v) N-lauroyl sarcosine and 0.37 mM xylene cyanol in 45 nM borate buffer at pH 9.3.

Another aspect of the present invention provides a method of providing uniform spot size and morphology in the production of an assay article for the detection of a biopolymer, said method comprising adding an aliquot of said biopolymer to an aliquot of a spotting solution comprising N-lauroyl sarcosine in a buffered solution.

Yet another aspect of this invention provides a means for non-destructive quality control of the production of a assay article for use in biopolymer detection, said method comprising mixing an aliquot of said biopolymer with an aliquot of a spotting solution comprising N-lauroyl sarcosine and a fluorophore or a dye in a buffered solution to provide a biopolymer solution.

Another aspect of the present invention provides a method of making an assay article for use in biopolymer detection, said method comprising:

(a) providing a solution of said biopolymer by mixing an aliquot of said biopolymer with an aliquot of a spotting solution, said spotting solution comprising N-lauroyl sarcosine in a buffered solution;

(b) providing a substrate;

(c) contacting said biopolymer solution with a surface of the substrate to provide one or more spots containing said target biopolymer on the surface of said substrate; and (d) incubating the substrate under conditions sufficient to allow said biopolymer to adsorb to the surface of the substrate.

In another embodiment of the present invention, a plurality of different biopolymers may be deposited and adsorbed on the surface of the substrate in an array. The substrate may be fabricated in a form of plates including multiple well microplates, sheets, films, slides, gels, membranes, beads, particles, foams, filaments, threads, and like structures.

The spotting solutions of this invention can be deposited onto the surface of a substrate using either contact or non-contact arraying technologies, and do not interfere with the attachment of biopolymers such as oligonucleotides to the substrate or affect hybridization intensity. In certain embodiments, the spotting solutions contain a fluorophore or a dye and therefore also serve as an easy and robust means for quality control of assay article production. In embodiments of this invention utilizing a spotting solution comprising a fluorophore or a dye, the assay article can be washed after the quality inspection process to remove the fluorophore or dye to eliminate background signal-to-noise intensities.

Yet another aspect of this invention provides a method of detecting a target biopolymer contained in a sample, said method comprising:
(a) providing a substrate;
(b) providing a probe biopolymer that can form a complex with the target biopolymer;
(c) combining either said probe or said target biopolymer with a spotting solution comprising N-lauroyl sarcosine in a buffered solution to form a dispensing solution;
(d) contacting said dispensing solution with a surface of said substrate to provide one or more spots containing said probe or said target biopolymer on the surface of said substrate;
(e) incubating said substrate under conditions sufficient to allow said probe or said target biopolymer to adsorb to the surface of said substrate to provide a probe assay article or a target assay article;
(f) contacting the probe assay article with said sample containing said target biopolymer or contacting said target assay article with said probe biopolymer under conditions that allow the formation of a complex comprising the probe and target biopolymer; and
(g) detecting the presence of said complex to determine the presence of said target biopolymer in said sample.

In accordance with another embodiment of this invention, the spotting solution further comprises a fluorophore or a dye, and step (e) further comprises evaluating the size and/or morphology of said spots.

Yet another aspect of this invention provides a test kit for detecting a target biopolymer contained in a sample, comprising a substrate and a spotting solution for dispensing a biopolymer onto a substrate, said solution comprising N-lauroyl sarcosine in a buffered solution.

The present invention is well suited for creating biopolymer arrays and polynucleotide arrays, such as gene expression micro-arrays for use in gene expression analysis, in particular. The polynucleotide arrays may be used for the evaluation or identification of biological activity. The present invention may also be used in creating polynucleotide arrays for the purpose of polynucleotide sequencing. Further, the assay articles of the present invention may contain a range of adsorbed biopolymers and may be utilized in hybridization assays and immunoassays.

The present invention provides many advantages. The spotting solutions of this invention provide an easy and inexpensive method of producing assay articles such as microarrays with uniform spot size and uniform morphology, and therefore provide high levels of accuracy and consistency in assays using such articles. The spotting solution can be dispensed onto a variety of substrates using either contact printing technologies or non-contact printing technologies. The spotting solutions do not interfere with the adsorption (attachment) of biopolymers to the substrate surface or affect the hybridization intensity during assays. Further, spotting solutions of this invention comprising a fluorophore or a dye provide an easy and robust means for quality control in the production of assay articles. After the quality inspection process, the fluorophore or dye can be completely washed out, eliminating any background noise to signal intensities.

Additional advantages and features of this invention shall be set forth in part in the description that follows, and in part will become apparent to those skilled in the art upon examination of the following specification or may be learned by the practice of the invention. The features and advantages of the invention may be realized and attained by means of the instrumentalities, combinations, and methods particularly pointed out in the appended claims.

BRIEF DESCRIPTION OF THE FIGURES

The accompanying drawings, which are incorporated in and form a part of the specification, illustrate non-limiting embodiments of the present invention, and together with the description serves to explain the principles of the invention.

In the drawings:

FIG. 1 is an assay image of an array printed using an inkjet-based arrayer onto a substrate with a spotting solution containing fluorescein and 0%, 0.0018%, or 0.045% (w/v) N-lauroyl sarcosine in borate buffer at pH 9.3.

FIGS. 2A-2D are assay images of an array printed using an inkjet-based arrayer onto a substrate with a spotting solution containing 0.37 mM xylene cyanol and varying amounts of formamide (FIG. 2A), betaine (FIG. 2B), dimethyl sulfoxide (FIG. 2C) or N-lauroyl sarcosine (FIG. 2D) in borate buffer (pH 9.3).

FIGS. 3A-3C are assay images of an array printed using an inkjet-based arrayer onto a substrate with various spotting solutions. The array in FIG. 3A was printed using a commercial formulation sold as Micro Spotting Solution Plus, FIG. 3B was printed using a spotting solution of this invention containing 0.0018% (w/v) N-lauroyl sarcosine and 0.37 mM xylene cyanol in borate buffer at pH 9.3, and in FIG. 3C the arrows indicate spots printed using a commercial formulation of a spotting solution sold as Genetix Aldehyde Microarray Spotting Solution.

FIG. 4A is an assay image of an array printed using an inkjet-based arrayer onto a substrate with a spotting solution containing 0.0018% (w/v) N-lauroyl sarcosine and 0.37 mM xylene cyanol in borate buffer at pH 10 (spots labeled with the number "3") or pH 10.5 (spots labeled with the number "4").

FIG. 4B is an assay image of an array printed using an inkjet-based arrayer onto a substrate with a spotting solution containing 0.0018% (w/v) N-lauroyl sarcosine and 0.37 mM xylene cyanol in borate buffer at pH 8.5 (spots labeled with the number "1") or pH 9.3 (spots labeled with the number "2").

FIGS. 5A and 5B are assay images of an array printed using an inkjet-based arrayer onto a substrate with a spotting solution containing 0.0018% (w/v) N-lauroyl sarcosine and 0.37 mM xylene cyanol in borate buffer at pH 9.3 and incubated at room temperature at 70% relative humidity (FIG. 5A) or 95% relative humidity (FIG. 5B).

FIG. 6 is an assay image of an array printed using a contact pin arrayer onto a substrate with a spotting solution containing 0.0018% (w/v) N-lauroyl sarcosine and 0.65 nM fluorescein in borate buffer (pH 9.3).

FIGS. 7A and 7B are assay images of an array printed using an inkjet-based arrayer onto a substrate with a spotting solution containing 0.0018% (w/v) N-lauroyl sarcosine and 40 nM fluorescein dye or 65 nM fluorescein dye in borate buffer (pH 9.3) and imaged either immediately after the arraying process (FIG. 7A) or after rinsing with a washing solution (FIG. 7B).

DETAILED DESCRIPTION OF THE INVENTION

One aspect of this invention provides spotting solutions for the production of assay articles for the detection of biopolymers, wherein the spots printed on said articles have uniform spot size and uniform morphology. More specifically, one aspect of this invention provides a spotting solution for depositing biopolymers onto a substrate, said solution comprising N-lauroyl sarcosine or equivalents thereof in a buffered solution. The present invention is based on the discovery that presence of N-lauroyl sarcosine (NLS) in the spotting solution provides assay articles having significantly improved uniformity in spot size and morphology. In alternative embodiments, the spotting solutions contain compounds that are modifications of N-lauroyl sarcosine and that can perform the same function as N-lauroyl sarcosine, and as such these modified compounds are considered to be equivalents of N-lauroyl sarcosine for purposes of this invention.

As used herein, the term "uniform spot size" means that the relative standard deviation (RSD) of the diameters of the spots deposited onto the substrate is less than 20%, preferably less than 10%, and more preferably less than 5%. The term "uniform morphology" as used herein means that the spots are consistent with a circular shape and the RSD of signal intensities within spots is less than 30%, preferably less than 20%, and more preferably less than 10%.

The term "spotting solution" refers to a solution with which an aliquot containing a biopolymer is mixed for dispensing or depositing discrete aliquot(s) of the biopolymer onto the surface of a substrate.

According to one embodiment of this invention, the spotting solution contains between about 0 and 0.045% (w/v) N-lauroyl sarcosine. In another embodiment, the solution contains about 0.0018% (w/v) N-lauroyl sarcosine. In yet another embodiment, a spotting solution of this invention comprises 0.0018% (w/v) N-lauroyl sarcosine and 0.37 mM xylene cyanol in 45 mM borate buffer at pH 9.3.

The N-lauroyl sarcosine is mixed with a suitable buffer solution, wherein the pH of the buffer is determined by the method or chemistry used to adsorb the biopolymer to the substrate. Accordingly, the pH of the buffer can be acidic, neutral, or basic. In one embodiment, the pH of the spotting solution is between about 8.5 and 10.5. For example, in one embodiment a borate buffer of pH 9.3 is mixed with the N-lauroyl sarcosine. Other suitable buffers are well known to those skilled in the art.

This invention is further based on the discovery that including a fluorophore or a dye in the spotting solution provides an easy and robust means of non-destructive quality control of assay article production. When a fluorophore or a dye is included in the spotting solution as described herein for quality control purposes, each printed spot can be examined prior to using the assay article to evaluate the size and morphology of the spots (also referred to in the art as "printed elements"). The ability to visualize the microdroplets substantially enhances the ability to perform quality control with respect to the assaying process. This leads to a substantial increase in value in the assaying methodology.

Accordingly, another aspect of this invention provides a spotting solution for binding biopolymers to a substrate, said solution comprising N-lauroyl sarcosine and a fluorophore or a dye in buffered solution. Examples of suitable fluorophores include, but are not limited to, fluorescein and derivatives thereof, and rhodamine and derivatives thereof. An example of a dye suitable for purposes of this invention includes, but is not limited to, xylene cyanol. The fluorophore or dye is present in an amount that will provide sufficient contrast for inspecting the printed spots. In one embodiment, the spotting solutions of this invention contain between about 0 and 65 nM fluorescein, preferably between about 45 and 65 nM fluorescein. In another embodiment, the spotting solutions contain about 0.37 mM xylene cyanol.

The spotting solutions of this invention are applicable in both contact and no-contact spotting technologies for the production of assay articles such as microarrays for the detection of biopolymers. For example, in one embodiment the spotting solutions of this invention may be for microdispensing of biopolymers for small-volume assays. As stated, the assay articles produced according to the methods of this invention are useful for the detection of biopolymers and other analytes of interest in a sample, including, but not limited to, cells, cellular fragments, tissues, drugs, small organic molecules, and carbohydrates, provided that the biopolymer, analyte, or a probe for the biopolymer or analyte can be fixed to the support and a detection probe or reagent for the analyte is available or can be prepared.

The term "biopolymer," as used herein, includes, but is not limited to, nucleic acids, peptides, polypeptides, carbohydrates, and analogues thereof. As used herein, the terms "nucleic acid," "polynucleotide," and oligonucleotide refer to a polymer of two or more modified or unmodified deoxyribonucleotides or ribonucleotides, either in the form of a separate fragment or as a component of a larger construction. Examples of polynucleotides include, but are not limited to, DNA, RNA, or DNA analogs, such as PNA (peptide nucleic acid), and any chemical modifications thereof. The DNA may be a single- or double-stranded DNA, cDNA, or a DNA amplified by PCR technique. The RNA may be an mRNA. The polynucleotide may be derived synthetically or by cloning.

As used herein, "peptide" refers to a polymer of amino acids chemically bound by amide linkages (CONH). An "amino acid" is defined as an organic molecule containing both an amino group ($NH_2$) and a carboxylic acid (COOH). As used herein, the term "peptide" includes peptides, polypeptides, and proteins. A protein may comprise one or multiple polypeptides, linked together by disulfide bonds. Examples of proteins include, but are not limited to, antibodies, antigens, ligands, receptors, etc.

As used herein, "carbohydrate" refers to polymers of the formula $C_n(H_2O)_n$ and includes disaccharides, trisaccharides, etc. as well as macromolecular polymeric substances, such as starch, glycogen, and cellulose polysaccharides.

Accordingly, another aspect of this invention relates to a method of making an assay article such as a microarray for use in biopolymer detection and to the articles prepared by such method. The method of making an assay article according to this invention comprises:

(a) providing a solution of said biopolymer by mixing an aliquot of said biopolymer in an aliquot of a spotting solution, said spotting solution comprising N-lauroyl sarcosine in a buffered solution;

(b) providing a substrate; and (c) contacting said biopolymer solution with a surface of the substrate; and (d) incubating said substrate under conditions that allow said biopolymer to adsorb onto said surface.

In accordance with another embodiment of this invention, the spotting solution may further comprises a fluorophore or a dye, and the method of making the assay article may further comprise:

(e) evaluating the assay article to determine the extent of uniformity in spot size and morphology.

After the assay article has been evaluated and determined to be suitable for use in an assay, the assay article is optionally washed to remove residual fluorophore or dye. It will be appreciated that once a spotting solution and spotting technique for dispensing a particular spotting solution onto a substrate surface has been optimized for depositing spots of uniform size and/or morphology, it may no longer be necessary include a fluorophore or a dye in the spotting solution as a means of quality control for that particular article production.

The spotting solutions of the present invention may be used to deposit uniform microdroplets onto almost any substrate. In order to accommodate a number of different testing techniques including specialized testing equipment, substrates may be molded into any of a variety of shapes and forms. Examples of such shapes and forms of the substrates include, but are not limited to, plates including multiple well microplates, sheets, films, slides, gels, membranes, beads, particles, foams, filaments, threads, and like structures. A substrate may be fabricated in the form of a planar device having discrete isolated areas in the form of wells, troughs, pedestals, hydrophobic or hydrophilic patches, die-cut adhesive reservoirs or other physical barriers to fluid flow. Examples of such a substrate include, but are not limited to, a microplate, or the like. Because the substrate of the present invention is particularly useful in the preparation of biopolymer arrays for the evaluation or identification of biological activity, the substrate is preferably in the form of a device having at least one flat planar surface. Examples of such devices with flat surfaces include, but are not limited to, plates, slides, sheets, films, or the like.

The substrate may be made of a variety of materials. For example, the substrate is made of crosslinked polymers including, but not limited to, polypropylene, polyethylene, polystyrene, and carboxylated polyvinylidene fluoride. In one embodiment, aminated polypropylene or polystyrene substrates are used. Other suitable substrates for purposes of this invention include, but are not limited to, nitrocellulose, nylon or other polymeric membrane materials, glass, silica, ceramic, gold or other metallic porous and non-porous materials, or porous foam, such as Porex polypropylene.

The size of the substrate can vary and depends upon the final use of the immobilized biopolymers. Those skilled in the art will appreciate that arrays of biopolymers immobilized on miniaturized solid supports have been under development for many years. These solid supports can be measured in terms of $mm^2$ and can have numerous different immobilized biopolymers, each attached to a different site-specific location on the miniaturized solid support. Solid supports in the form of dipsticks and slides are also within the scope of the present invention. As known in the art, dipsticks typically are rectangular in shape with each side measuring a few centimeters.

It was discovered that the particular method used to carry out the step of contacting the biopolymer with the substrate is not critical, as demonstrated in the Examples that follow. That is, both non-contact and contact arraying techniques will accommodate the spotting solutions of this invention. In accordance with embodiments of the present invention, the contacting step may be carried out using ink-jet systems, solid or open capillary device contact printing methods, solid pins, quill-pins, ring-and-pin systems, microfluidic channel printing, silk screening, and printing using devices based upon electrochemical or electromagnetic forces. Other suitable methods include thermal inkjet printing techniques utilizing commercially available jet printers and piezoelectric microjet printing techniques as described in U.S. Pat. No. 4,877,745, bubble-jet, syringe, and electo-kinetic methods. A Biomek High Density Replicating Tool (HDRT) (Beckman Coulter, Calif.) may also be used for an automatic gridding. Alternatively, the contacting step may be carried out by manual spotting of the biopolymers onto the surface of a substrate. Examples of manual spotting techniques include, but are not limited to, manual spotting with a pipettor.

The concentration of biopolymers contained in the spotting solutions of this invention may vary depending on the type of molecule, the molecule size, the molecule structure, and other factors that may influence solubility of the molecules. Preferably, the amount of the biopolymers applied to the surface of the substrate ranges from about $10^{-20}$ to about $10^{-14}$ moles. For example, in one embodiment, the biopolymer is a polynucleotide, and the amount of the polynucleotide applied to the substrate is about $10^{-18}$ moles. The size of the biopolymer solution aliquot is not crucial, as long as it provides sufficient amount of the biopolymer. Consequently, the size of the aliquots applied to the substrate surface may vary, depending on the concentration of the biopolymer in the solution and the assay needs. For example, the aliquot may be from about 0.1 nL to about 500 nL. In one embodiment, the biopolymer is a polynucleotide, and aliquots of about 10 nL of the 1 nM polynucleotide solutions are dispense onto the surface of a substrate.

Once the aliquots are dispensed onto the substrate, the target biopolymer(s) or target analyte(s) contained in each of the aliquots is immobilized onto the surface of the substrate. In one embodiment, the target is immobilized on the substrate surface by direct adsorption, as described in commonly assigned and co-pending U.S. patent application Ser. No. 09/694,701, filed Oct. 23, 2000 and entitled "Immobilization of Biopolymers to Aminated Substrates by Direct Adsorption," which is specifically incorporated herein by reference. In this embodiment, a target is immobilized on a substrate by contacting the target with the substrate under a condition sufficient for a direct adsorption of the target to the substrate. A condition is sufficient if it allows the target to become adsorbed on the surface of the substrate in a stable way. Here, the term "direct adsorption" means adsorption without any chemical linkers. In this embodiment, the target is immobilized on a substrate by simple air-drying on the substrate. The air-drying step is conducted for a period of time sufficient to allow adsorption of the target solution. The length of the air-drying time depends on the volume of the aliquots applied to the substrate, temperature, and humidity.

Alternatively, the target is immobilized on the substrate by indirect adsorption, that is, adsorption through chemical linkers, such as in the methods disclosed in U.S. Pat. Nos.

6,013,789 and 6,146,833, each of which is specifically incorporated herein by reference. For example, U.S. Pat. No. 6,013,789 describes immobilization of imidazole-activated nucleic acids to amino-polypropylene supports, and U.S. Pat. No. 6,146,833 describes immobilization to acyl fluoride activated supports.

In accordance with the present invention, the incubation step is conducted for a period of time sufficient to allow adsorption of the biopolymer or analyte to the surface of the substrate. The length of the incubation time depends on the volume of the aliquots applied to the substrate, and the temperature and humidity conditions during the incubation. The relative humidity is critical to certain immobilization chemistries. For example, in certain embodiments the lower limit for relative humidity is about 50%. In one embodiment, micro- and nanoliter aliquots are dispensed on the surface of the substrate, and the incubation step, which may comprise air-drying, may take from about 5 to about 60 minutes.

As mentioned above, many applications for utilizing immobilized biopolymers require biopolymers to be immobilized at site-specific locations on a substrate surface. Accordingly, in the present invention, a plurality of biopolymers may be placed and adsorbed on the surface of the substrate in an array format. In order to prepare ordered arrays of biopolymers with each biopolymer located at site-specific locations, including grids and 1×n arrays of immobilized biopolymers, a preselected site on the surface of the substrate is exposed to a solution of the desired biopolymer. In accordance with the present invention, this can be accomplished by contact arraying techniques such as manually applying an aliquot of biopolymer solution to a preselected location on the substrate. Alternatively, non-contact techniques such as thermal inkjet printing techniques utilizing commercially available jet printers or piezoelectric microjet printing techniques, as described in U.S. Pat. No. 4,877,745, which is incorporated herein by reference, can be utilized to spot selected substrate surface sites with selected biopolymers.

A wide variety of array formats may be employed in accordance with the present invention. One particularly useful format is a linear array of nucleic acid probes, such as that used in a device referred to in the art as a dipstick. Another suitable format comprises a two-dimensional pattern of discrete cells. For example, this invention is particularly suited for the production of microarrays comprising discrete, equivalent aliquots ("printed elements") of a sample on a substrate in a spatially defined and addressable manner such as a 1×n array. Of course, as would be readily appreciated by those skilled in the art, other array formats would be equally suitable for use in accordance with the present invention.

This invention further provides assay articles prepared by the method of this invention as described hereinafter in detail. The assay article of the present invention may be a part of a variety of devices, such microtiter plates, particles, test tubes, inorganic sheets, dipsticks, etc. For example, when the substrate is a thread, one or more of such threads can be affixed to a plastic dipstick-type device. When the substrate is in a form of a membrane, it can be affixed to glass slides. The particular device is, in and of itself, unimportant, as long as the substrate is securely affixed to the device without affecting the functional behavior of the substrate or any adsorbed biopolymer. The device should also be stable to any materials into which the device is introduced (e.g., clinical samples, etc.).

A biopolymer array article of the present invention may also be used as a device for performing a ligand binding assay or for performing a hybridization assay by either reverse hybridization (probes attached) or southern blot (target attached). Such a device may also be used in an immunoassay.

Accordingly, another aspect of the present invention provides a method of detecting a target biopolymer contained in a sample. The method comprises the steps of:
(a) providing a substrate;
(b) providing a probe biopolymer that can form a complex with the target biopolymer;
(c) combining either said probe or said target biopolymer with a spotting solution comprising N-lauroyl sarcosine in a buffered solution to form a dispensing solution;
(d) contacting said dispensing solution with a surface of said substrate to provide one or more spots containing said probe or said target biopolymer on the surface of said substrate;
(e) incubating said substrate from step (d) under conditions sufficient to allow said probe or said target biopolymer to adsorb to the surface of said substrate to provide a probe assay article or a target assay article;
(f) contacting the probe assay article with said sample containing said target biopolymer or contacting said target assay article with said probe biopolymer under conditions that allow the formation of a complex comprising the probe and target biopolymer; and
(g) detecting the presence of said complex to determine the presence of said target biopolymer in said sample.

In one embodiment, the spotting solution further comprises a fluorophore or a dye, and after the incubation step (e) the dispensed spots are evaluated for uniformity in spot size and morphology. As discussed above and further described in the Examples, the presence of a fluorophore or a dye provides a quick and efficient means for monitoring the quality of the size and morphology of the spots dispensed using a spotting solution of this invention, and thus provides an easy and non-destructive means for quality control in the production of assay articles. The printed spots are visualized with the naked eye or are imaged with an emission wavelength of the fluorophore subsequent to the dispensing process to inspect the spot sizes and shapes. Alternatively, the printed spots are visualized or imaged after incubating the printed substrate followed by washing the substrate to wash off residual fluorophore or a dye. The fluorophore or dye is present in the spotting solution in an amount that will provide sufficient contrast for inspecting the printed spots. In accordance with one embodiment of this invention, the spotting solutions of this invention contain between about 0 and 65 nM of fluorescein. In another embodiment, the spotting solutions contain between about 45 and 65 nM of fluorescein.

For the purpose of the present invention, the probe biopolymer recognizes and binds to the target biopolymer forming a probe-target complex. Both the probe and the target biopolymers may be selected from a group consisting of nucleic acids, polypeptides, proteins, and their analogues. For example, when the target is a polynucleotide, the probe may comprise a polynucleotide that is complimentary to the target polynucleotide. When the target is a receptor or a ligand, the probe may comprise a ligand or a receptor that respectively recognizes and binds to the target receptor or ligand. When the target is an antigen, the probe may comprise an antibody that recognizes the antigen, or vice versa.

Either the target or probe may be adsorbed on the surface of the substrate. For example, in the Southern blot or Northern blot applications, targets are adsorbed on the substrate. The substrate with the adsorbed targets is then contacted with the probes, which are preferably labeled, to detect the target biopolymers. In ligand binding assays or affinity purification assays, probes are bound to the substrate first, and the target contained in a sample solution is then contacted with the probes adsorbed on the substrate.

For the purpose of the present invention, an incubation condition is sufficient if the probe or target can adsorb on the substrate. Such a condition may vary, depending on the type of the biopolymers and their size. One skilled in the art can readily determine the suitable conditions for adsorbing other probes or targets in view of the teaching of the present invention.

Contacting the probes with the targets (or hybridization) is conducted under conditions that allow the formation of stable complexes between probes and targets. For example, when target polynucleotides are contacted with probe polynucleotides adsorbed on a substrate surface, complementary regions on the target and the probe polynucleotides anneal to each other, forming probe-target complex. The selection of such conditions is within the level of skill in the art and includes those in which a low, substantially zero, percentage of mismatched hybrids form. The precise conditions depend, however, on the desired selectivity and sensitivity of the assay. Such conditions include, but are not limited to, the hybridization temperature, the ionic strength and viscosity of the buffer, and the respective concentrations of the target and probe biopolymers. Hybridization conditions may be initially chosen to correspond to those known to be suitable in standard procedures for hybridization to filters and then optimized for use with the substrates of the present invention. The conditions suitable for hybridization of one type of target material would appropriately be adjusted for use with other target materials.

For example, in certain embodiments the target polynucleotides are hybridized to the probe polynucleotides at temperatures in the range of about 20° C. to about 70° C., for a period from about 1 hour to about 24 hours, in a suitable hybridization buffer. Suitable hybridization buffers for use in the practice of the present invention generally contain a high concentration of salt. A typical hybridization buffer contains in the range of about 2× to about 6×SSC and about 0.01% to about 0.5% SDS at pH 7-8. Once the probe/target complex is formed, the substrates are washed under conditions suitable to remove substantially all non-specifically bound target or probe biopolymers. Preferably, the washing is carried out at a temperature in the range of about 20° C.-70° C. with a buffer containing about 0.1-6×SSC and 0.01-0.1% SDS. The most preferred wash conditions for polynucleotides presently include a temperature, which is the same as hybridization temperature, and a buffer containing 2×SSC and 0.01% SDS. As previously noted, it would be a routine matter for those working in the field to optimize the contacting (hybridization) conditions for any given combination of target and probe biopolymers.

In accordance with embodiments of the present invention, either the targets or probes of the present invention may be labeled with a reporter. Detectability may be provided by such characteristics as color change, luminescence, fluorescence, or radioactivity. Examples of reporters include, but are not limited to, dyes, chemiluminescent compounds, enzymes, fluorescent compounds, metal complexes, magnetic particles, biotin, haptens, radio frequency transmitters, and radioluminescent compounds. One skilled in the art can readily determine the type of reporter to be used once the type of target or probe biopolymers is determined.

The labeling procedure may occur prior to analysis (direct labeling) or after hybridization (indirect labeling). An example of indirect labeling would be the biotinylation of a target polynucleotide, hybridizing it with a probe, and reacting the target-probe complexes with a streptavidin-alkaline phosphatase conjugate. The biotin moieties retained after the hybridization with probe polynucleotides bind to a streptavidin-alkaline phosphatase conjugate, which then acts on a chromogenic substrate, such as Enzyme Labeled Fluorescent (ELF) reagent.

For the purpose of the present invention, the same or different biopolymers may be attached to the substrates. For example, a substrate may be a microplate, and the biopolymers may be distributed within discrete wells in the form of an array. If the biopolymers are different, preferably they are located in isolated areas of the substrate to form arrays. In accordance with another embodiment of the present invention, the substrate may be a slide and different biopolymers are adsorbed on different areas of the slide to form an array.

The signal produced by an array may be detected by the naked eye or by means of a specially designed instrumentation, such as a confocal array reader. For example, in one embodiment, a fluorescent signal is recorded with a charged coupled device (CCD) camera. It would be appreciated by those skilled in the art, that the choice of a particular method used to detect and quantify the signal is not crucial for this invention. Essentially, any detection method may be used as long as it provides consistent and accurate results.

It will be appreciated that this method allows for rapid and economical screening of a large number of targets in a single sample. For example, in one embodiment the spotting solutions of this invention may be for microdispensing of biopolymers for small-volume assay for the detection of the biopolymers including, but not limited to, nucleic acids, proteins, antibodies, haptens, polypeptides, and carbohydrates in a single sample. A "sample" refers to a substance that is being assayed for the presence of one or more target biopolymers and/or analytes of interest and includes, but is not limited to, cells, cellular fragments, tissues, drugs, small organic molecules, and carbohydrates. In one embodiment, the target biopolymer is a specific nucleic acid sequence, e.g., a portion of a nucleic acid, a particular gene, or a genetic locus in a genomic DNA known to be involved in a pathological condition or syndrome.

Another aspect of the present invention provides a test kit for detecting a target biopolymer contained in a sample. The kit comprises a substrate and a spotting solution of this invention comprising N-lauroyl sarcosine in a buffered solution. In accordance with another embodiment of this invention, the spotting solution may further comprise a fluorophore or a dye. The kit may also include a reporter for generating a signal, which indicates formation of the complex.

The invention may be better understood with reference to the accompanying examples that are intended for purposes of illustration only and should not be construed as, in any sense, limiting the scope of the present invention, as defined in the claims appended hereto. While the described procedures in the following examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Effect of Concentration of N-Lauroyl Sarcosine on Spot Size and Morphology

The amount of N-lauroyl sacrosine (NLS) needed to provide an effective spotting solution was investigated. Three different spotting solutions were prepared with 37 mM xylene cyanol in 45 mM borate buffer (pH 9.3) and either 0.045% (w/v) NLS, 0.0018% (w/v) NLS, or no NLS. Each of the three solutions were combined with IL6, TNF, IL10, and IL2, and then spotted on a 96-well plate using an inkjet-based arrayer. Table 1 summarizes the dependence of the Correlation of Variance (CV's) of signal intensities in each assay on the concentration of NLS. The CV's of the signal intensities with assay were lower when a concentration of 0.0018% (w/v) NLS was used in the spotting solution compared to the absence of NLS in the spotting solutions. However, with a higher concentration of 0.045% (w/v) NLS, the CV's were higher, mainly due to the diffused and enlarged spot shapes with higher concentrations of NLS. FIG. 1 shows an image of the array, and illustrates that the use of NLS at a concentration of 0.0018% (w/v) significantly improves the uniformity in spot size and morphology.

TABLE 1

| Concentration of NLS | CV of Signal Intensity with Assay* | | |
|---|---|---|---|
| | 0.045% | 0.0018% | 0% |
| IL6 | 28 | 15 | 25 |
| TNF | 29.5 | 10.5 | 5 |
| IL10 | 14 | 4 | 25 |
| IL12 | 10.5 | 7 | 5 |
| Average | 21 | 9 | 15 |

*Total of 12 data points

EXAMPLE 2

Comparison of N-Lauroyl Sarcosine with Known Chemicals on the Effect of Spot Size and Morphology in Spot Arraying N-lauroyl sacrosine was compared with other chemicals used in the art for improving spot size and morphology in spotting solutions. Several spotting solutions were prepared with (1) formamide, (2) betaine, (3) DMSO, or (4) N-lauroyl sacrosine and 0.37 mM xylene cyanol in 45 mM borate buffer (pH 9.3). The assay images of the arrays printed on a 96-well plate using the various spotting solutions an inkjet-based arrayer are shown in FIGS. 2A-2D. FIG. 2A shows the results for the spotting solution containing 10%, 20%, or 30% (v/v) formamide, FIG. 2B shows the results for the spotting solution containing 1%, 2%, or 4% (w/v) betaine, FIG. 2C shows the results for the spotting solution containing 0%, 10%, or 20% (v/v) dimethyl sulfoxide, and FIG. 2D shows the results for the spotting solution containing 0.0018% (w/v) N-lauroyl sacrosine. While formamide, betaine, and DMSO were found to improve the morphology of the dispensed spots to some extent, the signal intensities of these spots were found to be significantly lower that those spotted with the spotting solution containing 0.018% (w/v) NLS. The weaker signals might be attributed to the interferences of the chemicals with the attachment chemistry of the dispensed reagents to the microarray substrate.

EXAMPLE 3

Comparison of Spotting Solution Containing N-Lauroyl Sarcosine with Spotting Solutions on the Effect of Spot Size and Morphology in Spot Arraying A spotting solution of this invention containing 0.0018% (w/v) N-lauroyl sacrosine and 0.37 mM xylene cyanol in 45 mM borate buffer (pH 9.3) was compared with two commercial formulations of spotting solutions sold as Micro Spotting Solutions Plus (Catalog No. MSP; TeleChem International, Inc., Sunnyvale, Calif.) and Genetix Aldehyde Microarray Spotting Solution (Catalog No. K2055; Genetix Reagents, St. James, N.Y.). All of the solutions were spotted on a 96-well plate using an inkjet-based arrayer. As shown in the array images in FIGS. 3A-C, the spotting solution of this invention containing 0.0018% (w/v) NLS (FIG. 3B) was found to be superior to MicroSpotting Solution Plus (FIG. 3A) and Genetix Aldehyde Microarray Spotting Solution (FIG. 3C) in providing array spots having more uniform spot size and morphology. In FIG. 3C, the spots printed with the Genetix Aldehyde Microarray Spotting Solution are indicated by the arrows.

EXAMPLE 4

Effect of pH of Spotting Solution and Humidity Levels During Post-Spotting Incubation on Spot Size and Morphology In microarraying processes, the pH of the spotting solution and the incubation conditions post-spotting are important factors affecting the bonding of the biopolymer to the substrate during the incubation step. Therefore, the applicability of a spotting solution of this invention containing 0.0018% (w/v) N-lauroyl sarcosine and 0.37 mM xylene cyanol at different solution pH's and incubated at different degrees of humidity was investigated. All solutions were printed on a 96-well plate using an inkjet-based arrayer.

FIG. 4A is an assay image of an array printed using an inkjet-based arrayer onto a substrate with a spotting solution containing 0.0018% (w/v) N-lauroyl sarcosine and 0.37 mM xylene cyanol in borate buffer at pH 10 (spots labeled with the number "3") or pH 10.5 (spots labeled with the number "4").

FIG. 4B is an assay image of an array printed using an inkjet-based arrayer onto a substrate with a spotting solution containing 0.0018% (w/v) N-lauroyl sarcosine in borate buffer at pH 8.5 (spots labeled with the number "1") or pH 9.3 (spots labeled with the number "2"). As shown, an array having uniform spot size and morphology can be achieved with spotting solutions of this invention having pH's in the range of at least 8.5 to 10.5.

FIGS. 5A and 5B show the assay images of spots printed with a spotting solution containing 0.0018% (w/v) of N-lauroyl sacrosine and 0.37 mM xylene cyanol in 45 mM borate buffer (pH 9.3). The solution was printed on the substrates using an inkjet-based arrayer. After spotting, the microarrays were incubated at room temperature at a relative humidity of either 70% (FIG. 5A) or 95% (FIG. 5B). As shown, an array printed with a spotting solutions of this invention can be incubated at various humidity levels and still provide arrays having uniform spot size and morphology.

EXAMPLE 5

Microarrays Prepared by Contact Dispensing Techniques

The microarrays prepared as described in Examples 1-4 were generated using an inkjet-based arrayer (i.e., non-contact dispensing technique). It is well known that the type of spot dispensing (i.e., contact or non-contact dispensing techniques) can have a high impact on spot morphology and homogeneity. In this example, the applicability of a spotting formulation of this invention to contact dispensing techniques was evaluated. FIG. 6 shows an assay image of arrays printed on a 96-well plate with a spotting solution containing 0.0018% (w/v) of N-lauroyl sacrosine and 65 nM fluorescein in 45 mM borate buffer (pH 9.3) using a contact pin arrayer. The excellent morphology and consistent spot sizes shown in FIG. 6 indicate that the spotting solution can be applied using a contact dispensing techniques as well as non-contact dispensing techniques.

EXAMPLE 6

Effect of Fluorescein Concentration

In order to monitor the quality of spotting using the spotting solutions of this invention, trace amounts (i.e., 45 nM or 65 nM) of fluorescein were added o the spotting solutions containing 0.0018% (w/v) N-lauroyl sacrosine and 45 mM borate buffer (pH 9.3). These solutions were then printed onto a 96-well plate. Spot defects, including spot coalescence, missing spots, mis-positioned spots, and inconsistent spot sizes can be easily detected before an assay is performed with the microarray. In the microarray shown in FIG. 7A, the printed spots were imaged with emission wavelength of fluorescein (525 nm) right after the dispensing process to inspect the spot sizes and shapes. As shown in FIG. 7A, the presence of 40 nM or 65 nM of fluorescein in the spotting solution provided images with good contrast for inspecting the printed spots. In this case, it was observed that images of spots prepared with solutions containing 65 nM fluorescein provided better contrast than those containing 40 mM fluorescien.

In order to reduce the contribution of signal noise from fluorescein to the biological assay, a similar microarray was prepared as above but was then rinsed with a washing solution containing 0.1% casein and 0.15 M NaCl in 50 nM carbonate buffer and then rinsed with water before imaged. The washed microarray was imaged at 525 nm and is shown in FIG. 7B. No residual signal from fluorescein was observed in the array shown in FIG. 7B, indicating that fluorescein can be completely washed out.

EXAMPLE 7

Effect of Fluorescein Concentration in Signal Intensities of Assay

Table 2 shows the comparison of signal intensities of an assay on microarrays spotted with a spotting solution containing 0.0018% (w/v) N-lauroyl sacrosine, 45 mM borate buffer (pH 9.3), and either 65 nM fluorescein or no fluorescein. The insignificant differences in the signal intensities between spots prepared with spotting solutions containing no fluorescein and those containing 65 nM fluorescein indicates that the addition of fluorescein in the spotting solution does not interfere with the bonding reaction of the biopolymer to the substrate or alternate further interactions. Thus, in addition to providing uniform spot size and morphology, spotting solutions of this invention containing NLS and fluorescein can also be used for non-destructive monitoring of the array spotting quality.

TABLE 2

| Concn. of | Spotting solution without fluorescein | | Spotting solution with 65 nM fluorescein | |
|---|---|---|---|---|
| IL-1b analyte (pg/mL) | Average of Signal Intensity* | Std. Deviation of Signal Intensity* | Average of Signal Intensity* | Std. Deviation of Signal Intensity* |
| 4357 | 152.6 | 22.3 | 150.7 | 5.8 |
| 871.4 | 104 | 9.1 | 91.1 | 14.7 |
| 174.3 | 40 | 2.3 | 37.5 | 3.2 |
| 34.9 | 10.7 | 0.4 | 10.7 | 0.6 |
| 7 | 3.3 | 0.2 | 3.2 | 0.3 |

*Total of 24 data points

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come within the meaning and range of the equivalence of the claims are to be embraced within their scope.

We claim:

1. A spotting solution for dispensing a biopolymer onto the surface of a substrate, comprising:

0.0018% (w/v) of N-lauroyl sarcosine and 65 nM fluorescein in 45 mM borate buffer at pH 9.3, such that the fluorescein does not affect the binding of said biopolymer to its probe or target in an assay of said biopolymer; and said biopolymer.

2. A spotting solution for dispending a biopolymer onto the surface of a substrate, comprising:

0.0018% (w/v) of N-lauroyl sarcosine and 0.37 mM xylene cyanol in 45 mM borate buffer at pH 9.3, such that the xylene cyanol does not affect the binding of said biopolymer to its probe or target in an assay of said biopolymer; and said biopolymer.

3. A spotting solution for dispensing a biopolymer onto the surface of a substrate, said solution comprising:
   0.0018% (w/v) of N-lauroyl sarcosine in a basic buffer solution, wherein said basic buffer solution has a pH between about 8.5 and 10.5;
   a fluorophore or dye, wherein said fluorophore or dye does not affect the binding of said biopolymer to its probe or target in an assay of said biopolymer; and
   said biopolymer.

4. A test kit for detecting a target biopolymer contained in a sample, comprising:
   a spotting solution for dispensing a probe biopolymer onto a substrate, said spotting solution comprising 0.0018% (w/v) of N-lauroyl sarcosine in a buffered solution, wherein said buffer solution has a pH between about 8.5 and 10.5;
   said probe biopolymer;
   a fluorophore or dye, wherein said fluorophore or dye does not affect the binding of said probe biopolymer to its target in an assay of said biopolymer; and
   said substrate.

5. A test kit for detecting a target biopolymer contained in a sample, comprising:
   a spotting solution for dispensing a probe biopolymer onto a substrate, said spotting solution comprising 0.0018% (w/v) of N-lauroyl sarcosine and 65 nM fluorescein in 45 mM borate buffer at pH 9.3;
   said probe biopolymer, wherein the fluorescein does not affect the binding of the probe biopolymer to its target in an assay of the biopolymer; and
   said substrate.

6. A test kit for detecting a target biopolymer contained in a sample, comprising:
   a spotting solution for dispensing a probe biopolymer onto a substrate, said spotting solution comprising 0.0018% (w/v) of N-lauroyl sarcosine and 0.37 mM xylene cyanol in 45 mM borate buffer at pH 9.3;
   said probe biopolymer, wherein the xylene cyanol does not affect the binding of the probe biopolymer to its target in an assay of the biopolymer; and
   said substrate.

* * * * *